United States Patent
Lu et al.

(10) Patent No.: US 6,927,031 B2
(45) Date of Patent: Aug. 9, 2005

(54) METHODS FOR IDENTIFYING POLYPEPTIDE FACTORS INTERACTING WITH RNA

(75) Inventors: Henry Lu, Foster City, CA (US); Weiqun Li, San Mateo, CA (US); David Anderson, San Bruno, CA (US)

(73) Assignee: Rigel Pharmaceuticals, Incorporated, South San Francisco, CA (US)

( * ) Notice: Subject to any disclaimer, the term of this patent is extended or adjusted under 35 U.S.C. 154(b) by 328 days.

(21) Appl. No.: 10/122,675

(22) Filed: Apr. 12, 2002

(65) Prior Publication Data

US 2003/0194712 A1 Oct. 16, 2003

(51) Int. Cl.$^7$ .................. C12Q 1/68; C12Q 1/70; C12Q 1/02; G01N 1/30; C12N 5/00
(52) U.S. Cl. .................. 435/6; 435/5; 435/29; 435/40.5; 435/325; 435/339
(58) Field of Search .................. 435/6, 5, 29, 40.5, 435/325, 339

(56) References Cited

U.S. PATENT DOCUMENTS 5,834,184 A   11/1998   Harada et al.
5,989,814 A   11/1999   Frankel et al.

FOREIGN PATENT DOCUMENTS

WO      WO 01/48480 A1    5/2001

OTHER PUBLICATIONS

Johnannes et al, Cap–independent polysomal association of natural mRNAs encoding c–myc, BiP, and eIF4G conferred by internal ribosome entry sites (1998) RNA, 4:1500–1513, p. 1500, Introduction, p. 1501, Results.*

Hellen et al., "Internal ribosome entry sites in eukaryotic mRNA molecules," *Genes & Development*, 15:1593–1612 (2001).

Kaminski et al., "Direct evidence that polyprimidine tract binding protein (PTB) is essential for Internal initiation of translation of encephalomyocarditis virus RNA," *RNA*, 1:924–938 (1995).

Bachler et al., "Strepto Tag: A novel method for the isolation of RNA–binding proteins," *RNA*, 5:1509–1516 (1999).

Hunt et al., "unr, a cellular cytoplasmic RNA–binding protein with five cold–shock domains, is required for internal initiation of translation of human rhinovirus RNA," *Genes and Development*, 13:437–448 (1999).

Lee et al., "Definition of the minimal viral components required for the initiation of unprimed RNA synthesis by influenza virus RNA polymerase," *Nucleic Acids Research*, 30:429–438 (2002).

Mehta et al., "A Sequence–Specific RNA–Binding Protein Complements Apobec–1 To Edit Apolipoprotein B mRNA," *Molecular and Cellular Biology*, 18:4426–4432 (1998).

Rodgers et al., "Use of Biotin–Labeled Nucleic Acids for Protein Purification and Agarose–Based Chemiluminescent Electromobility Shift Assays," 277:254–259 (2000).

Walter et al., "Differential utilization of poly(rC) binding protein 2 in translation directed by picornavirus IRES elements," *RNA*, 5:1570–1585 (1999).

Amfre Group, Cyanogen–Bromide, Chapter 5. Techniques of Protein Purification, 86.

Chan, Ray, "RNA Affinity Chromatography—Mar. 17, 1997," *Protocols: RNA affinity column*.

Min et al., "Identification of a Protein Complex That Binds to a Dodecamer Sequence Found at the 3' Ends of Yeast Mitochondrial mRNAs," *Molecular and Cellular Biology*, 13:4167–4173 (1993).

Kimura et al., Formation of a Carboxy–Terminal Domain Phosphatase (Fcp1)/TFIIF/RNA Polymerase II (pol II) Complex in *Schizosaccharomyces pombe* Involves Direct Interaction between Fcp1 and Rpb4 Subunit of pol II, *Molecular and Cellular Biology*, 22:1577–1588 (2002).

* cited by examiner

Primary Examiner—Hankyel T. Park
(74) Attorney, Agent, or Firm—Townsend and Townsend and Crew LLP

(57) ABSTRACT

The present invention relates to methods of screening for target polypeptides that bind to RNA, using affinity purification methods, and the use of such target polypeptide for drug discovery and in methods of treating and preventing disease, e.g., HCV infection.

63 Claims, No Drawings

SEQUENCE LISTING

<160> NUMBER OF SEQ ID NOS: 29

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:biotin
      labeled
      DNA oligonucleotide
<220> FEATURE:
<221> NAME/KEY: modified_base
<222> LOCATION: (1)
<223> OTHER INFORMATION: n = 5' phosphorylated a
<220> FEATURE:
<221> NAME/KEY: modified_base
<222> LOCATION: (15)..(19)
<223> OTHER INFORMATION: n = biotinylated t
<220> FEATURE:
<221> NAME/KEY: modified_base
<222> LOCATION: (20)
<223> OTHER INFORMATION: n = g bound to 3' terminator

<400> SEQUENCE: 1
nacagctatg accangannn                                              20

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:biotin
      labeled
      DNA oligonucleotide

```
<220> FEATURE:
<221> NAME/KEY: modified_base
<222> LOCATION: (1)
<223> OTHER INFORMATION: n = 5' phosphorylated c
<220> FEATURE:
<221> NAME/KEY: modified_base
<222> LOCATION: (24)
<223> OTHER INFORMATION: n = g bound to biotin with a 15 atom linker

<400> SEQUENCE: 2
ngctagccag cttgggtctc ccan                                              24

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:40S
      ribosomal
      protein S19 peptide

<400> SEQUENCE: 3

Asp Val Asn Gln Gln Glu Phe Val Arg
 1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence:YVH1 dual
      specificity phosphatase 12 peptide

<400> SEQUENCE: 4

Met Thr Pro Ser Ser Met Leu Thr Thr Gly Arg
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence:40S
      ribosomal
      protein S18 peptide

<400> SEQUENCE: 5

Ala Gly Glu Leu Thr Glu Asp Glu Val Glu Arg
 1               5                  10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence:40S
      ribosomal
      protein S18 peptide

<400> SEQUENCE: 6

Leu Arg Glu Asp Leu Glu Arg
 1               5

<210> SEQ ID NO 7
<211> LENGTH: 11
<212> TYPE: PRT
<213> ORGANISM: Artificial Sequence
```

```
<220> FEATURE:
<223> OTHER INFORMATION: Description of Artificial
      Sequence:survival/evasion peptide (DSEP, AIDD or
      preproteolysin) peptide

<400> SEQUENCE: 7

Glu Asn Ala Gly Glu Asp Pro Gly Leu Ala Arg
 1               5                  10

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence:40S
      ribosomal
      protein S7 (S8) peptide

<400> SEQUENCE: 8

His Val Val Phe Ile Ala Gln Arg
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence:40S
      ribosomal
      protein S7 (S8) peptide

<400> SEQUENCE: 9

Ile Leu Pro Lys Pro Thr Arg
 1               5

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:40S
      ribosomal
      protein S7 (S8) peptide

<400> SEQUENCE: 10

Val His Leu Asp Lys Ala Gln Gln Asn Asn Val Glu His Lys
 1               5                  10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence:40S
      ribosomal
      protein S7 (S8) peptide

<400> SEQUENCE: 11

Leu Leu Pro Gln Leu Leu Lys
 1               5

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence:40S
      ribosomal
      protein S7 (S8) peptide
```

```
<400> SEQUENCE: 12

Glu Leu Asn Ile Thr Ala Ala Lys
 1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence:40S
      ribosomal
      protein S5 peptide

<400> SEQUENCE: 13

Gln Ala Val Asp Val Ser Pro Leu Arg
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence:40S
      ribosomal
      protein S5 peptide

<400> SEQUENCE: 14

Tyr Leu Pro His Ser Ala Gly Arg
 1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence:40S
      ribosomal
      protein S5 peptide

<400> SEQUENCE: 15

Phe Thr Pro Ser Ser Phe Leu Lys
 1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence:40S
      ribosomal
      protein S5 peptide

<400> SEQUENCE: 16

Ala Ser Ser Pro Gly Tyr Ile Asp Ser Pro Thr Tyr Ser Phe
 1               5                  10

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:40S
      ribosomal
      protein L24 homologue peptide

<400> SEQUENCE: 17

Ala Gln Arg Glu Gln Ala Ile Arg
 1               5
```

```
<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:$0S
      ribosomal
      protein S3 peptide

<400> SEQUENCE: 18

Gly Leu Cys Ala Ile Ala Gln Ala Glu Ser Leu Arg
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:hypothetical
      protein DKFZp434A062.1 peptide

<400> SEQUENCE: 19

Leu Ile Leu Leu Ala Pro Gly Ser Ser Thr Gly Arg
 1               5                  10

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence:DNA
      fragmentation factor (DFF) alpha subunit peptide

<400> SEQUENCE: 20

Ser Lys Ala Cys Asp Ile Leu Ala Ile Asp Lys
 1               5                  10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence:
      transmembrane protein 7 peptide

<400> SEQUENCE: 21

Pro Asp Lys Gly Leu Leu Pro Asn Val Leu Lys
 1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence:actin
      peptide

<400> SEQUENCE: 22

Arg Val Ala Pro Glu Glu His Pro Val Leu Leu
 1               5                  10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence:actin
      peptide
```

-continued

```
<400> SEQUENCE: 23

Gly Tyr Ser Phe Thr Thr Thr Ala Glu Arg
 1               5                  10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence:laminin
      binding protein peptide

<400> SEQUENCE: 24

Ala Ile Val Ala Ile Glu Asn Pro Ala Asp
 1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence:laminin
      binding protein peptide

<400> SEQUENCE: 25

Met Ala Ala Asn Tyr Ser Ser Thr Ser Thr Arg
 1               5                  10

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence:elongation
      factor 2 (EF2) kinase peptide

<400> SEQUENCE: 26

Arg Gly Glu Leu Asp Asp Pro Glu Pro Arg
 1               5                  10

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence:tafazzin
      peptide

<400> SEQUENCE: 27

Glu Val Leu Tyr Glu Leu Ile Glu Lys
 1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence:inosine
      monophosphate dehydrogenase (IMPDH) peptide

<400> SEQUENCE: 28

Ile Lys Val Ala Gln Gly Val Ser Gly Ala
 1               5                  10
```

-continued

```
<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:inosine
      monophosphate dehydrogenase (IMPDH) peptide

<400> SEQUENCE: 29

Val Gln Asp Lys Gly Ser Ile His Lys
 1               5
```

METHODS FOR IDENTIFYING POLYPEPTIDE FACTORS INTERACTING WITH RNA

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to methods of screening for target polypeptides that bind to RNA, using affinity purification methods, and the use of such target polypeptide for drug discovery and in methods of treating and preventing disease, e.g., HCV infection.

BACKGROUND OF THE INVENTION

RNA-polypeptide interactions are essential for fundamental cellular and viral activities such as transcription and translation. Accordingly, significant effort has been expended to develop methods of identifying polypeptide factors that interact with RNA. Convenient and sensitive systems to effectively identify polypeptide factors that interact with RNA are being sought. One approach has focused on affinity purification of polypeptides using RNA sequences fused to affinity labels or tags. Affinity labels are typically able to bind to cognate ligand molecules thus providing a means for separating the tagged RNA molecule from a mixture.

For example, Hunt et al., Genes and Dev. 13:437–438 (1999) and others have described a procedure for covalently linking RNA to cyanogen bromide activated sepharose through a free amine group available on the RNA. Polypeptides that bound to the RNA sequence were identified by exposing the sepharose-linked RNA to cellular extract (see, e.g., Brown et al., J. Biol. Chem. 275 (10): 7424–72429 (2000); Kaminski et al., RNA 1:924–938 (1995). In a related method, Walter et al., RNA 5:1570–1585 (1999) described the use of agarose-adipic acid hydrazide to immobilize oxidized RNA and identify RNA binding proteins.

Lee et al., Nucleic Acids Res. 30(2): 429–438 (2002) and others (see, e.g., Rodgers et al., Anal. Biochem. 277(2): 254–259 (2000); Mehta et al., Mol. and Cell. Biol. 18(8): 4426–4432(1998)) have identified RNA binding polypeptides using a biotin linked RNA and affinity purification using streptavidin columns.

Finally, Bachler et al., RNA 5(11): 1509–1516 (1999) have identified RNA binding polypeptides using an heterologous RNA fused to a RNA aptamer sequence that binds to streptomycin, which is immobilized on sepharose beads (see also WO 01/48480).

There is a need, however, to further develop a novel, convenient and sensitive systems to effectively identify polypeptide factors that interact with RNA.

SUMMARY OF THE INVENTION

The present invention relates to novel affinity purification assays for polypeptide factors that interact with a RNA, e.g., a viral or cellular RNA. Such polypeptide factors are targets for drug discovery for therapeutic compounds for treatment of disease, e.g., small organic molecules, nucleic acids, antisense molecules, RNAi, ribozymes, lipids, antibodies, peptides, and circular peptides.

In one aspect, the present invention provides a method of screening for polypeptides that bind to an RNA, the method comprising the steps of: (i) incubating an affinity-labeled RNA with a cytoplasmic extract, wherein the RNA is linked to an affinity-labeled oligonucleotide; (ii) isolating the affinity-labeled RNA; and (iii) identifying polypeptides bound to the affinity-labeled RNA.

In another aspect, the present invention provides a method of screening for polypeptides that bind to an RNA, the method comprising the steps of: (i) incubating an affinity-labeled RNA with a cellular extract, wherein an amine group of a ribonucleotide base of the RNA is linked via a linker to a biotin molecule or polypeptide affinity label;
  (ii) isolating the affinity-labeled RNA; and (iii) identifying polypeptides bound to the affinity-labeled RNA.

In another aspect, the present invention provides a method of screening for polypeptides that bind to an RNA comprising an IRES, the method comprising the steps of: (i) incubating an affinity-labeled RNA with a cytoplasmic extract, wherein an amine group of a ribonucleotide base of the RNA is linked to an affinity label or wherein the 3' or 5' phosphate of the RNA is linked to an affinity label, and wherein the RNA comprises an IRES sequence; (ii) isolating the affinity-labeled RNA; and (iii) identifying polypeptides bound to the affinity-labeled RNA.

In another aspect, the present invention provides a method of screening for polypeptides that bind to an RNA comprising an IRES, the method comprising the steps of: (i) incubating an affinity-labeled RNA with a cytoplasmic extract, wherein the RNA is linked to an affinity-labeled oligonucleotide, and wherein the RNA comprises an IRES sequence; (ii) isolating the affinity-labeled RNA; and (iii) identifying polypeptides bound to the affinity-labeled RNA.

In one embodiment, the affinity label is biotin. In another embodiment, the polypeptide affinity label is selected from the group consisting of a peptide epitope, an antibody molecule, and a hexa-histidine peptide. In another embodiment, the polypeptide affinity label is a peptide epitope. In another embodiment, the peptide epitope is selected from the group consisting of myc, flag, and influenza hemagglutinin.

In one embodiment, the linker molecule is selected from the group consisting of an amino acid linker and an amino hexanoyl linker.

In one embodiment, the RNA comprises an IRES sequence. In another embodiment, the RNA is a cellular or a viral RNA. In another embodiment, the cellular RNA encodes a human protein selected from the group consisting of antennapedia, ultrabithorax, N-myc, c-myc, myt2, AML1/RUNX1, Gtx, c-jun, Mnt, Nkx6.1, NRF, YAP1, La autoantigen, eIF4GI, TIF4631, p97/DAP5/NAT1, XIAP, Apaf-1, BAG-1, Bip/GRP78, FGF-2, PDGF2/c-Sis, VEGF-A, estrogen receptor alpha, IGF-1 receptor, Notch2, connexin 43, connexin 32, Cyr61, ARC, MAP2, protein kinase $p_{58}^{PITSLRE}$, pim-1, alpha-CaM kinase II, CDK inhibitor p27, KV.14, beta F1-ATPase, Cat-1, ODC, dendrin, neurogranin/RC3, NBS1, FMR1, and RBM3. In another embodiment, the viral RNA is selected from the group consisting of a flavivirus, a retrovirus, a picornavirus, a tombarnovirus, or a herpes virus. In another embodiment, the retrovirus RNA is an HIV RNA. In another embodiment, the picomavirus RNA is a rhinovirus, a hepatovirus, an enterovirus, a poliovirus, a cardiovirus, an encephalomyocarditis virus, an aphtovirus, a foot and mouth disease virus, or a parechovirus. In another embodiment, the flavivirus RNA is an HCV RNA. In another embodiment, the HCV RNA comprises a HCV 5' untranslated region or a HCV 3' untranslated region. In another embodiment, the 5' untranslated region comprises an HCV IRES. In another embodiment, the 3' untranslated region comprises a polypyrimidine tract.

In one embodiment, the RNA is isolated using an affinity label ligand linked to a bead, a plate or a column. In another embodiment, the bead is an agarose bead or a magnetic bead.

In one embodiment, the cellular extract is from a cultured human cell. In one embodiment, the cultured cell is a hepatocyte or a lymphocyte. In another embodiment, the cellular extract is from a primary human cell. In another embodiment, the primary cell is a hepatocyte or a lymphocyte.

In one embodiment, the polypeptide is identified by proteolytic digestion and mass spectrometry analysis or in-gel proteolytic digestion and mass spectrometry analysis.

In one embodiment, the oligonucleotide is a DNA oligonucleotide or a DNA analog oligonucleotide. In one embodiment, the oligonucleotide is 5–40 bases in length.

In one embodiment, the oligonucleotide is covalently linked to the RNA In one embodiment, the RNA is covalently linked to the oligonucleotide by ligation of the oligonucleotide at the 3' end of the RNA.

In one embodiment, the oligonucleotide is non-covalently linked to the RNA. In another embodiment, the oligonucleotide is hybridized to the RNA at a complementary region at the 3' end of the RNA.

BRIEF DESCRIPTION OF THE DRAWINGS

Not applicable.

DETAILED DESCRIPTION OF THE INVENTION

Introduction

The invention provides convenient methods of screening for polypeptides that bind to RNA using an affinity-labeled RNA that is easily separated from solutions and mixtures. In a preferred embodiment, the target RNA is hybridized or ligated to an affinity labeled oligonucleotide, e.g., a biotin-labeled oligonucleotide. The affinity label allows the RNA to be immobilized on solid support. To screen for potential polypeptides that bind to the RNA, the immobilized affinity-labeled RNA is contacted with a cell lysate and subsequently washed with buffer. The cellular lysate can be from tissue, primary cultured cells, cultured cell lines, virally infected cells, or cells that are competent to support a viral infection. The lysates can be whole cell lysates, cytoplasmic extracts, or nuclear extracts. Preferably, mammalian or human cell extracts are used. Finally, polypeptides bound to the RNA are identified using proteomic techniques such as gel purification and/or mass spectrometry. The invention further provides methods for affinity-labeling the RNA at an amine moiety on the nucleoside base of the RNA, through the 3' or 5' phosphate group of the RNA, or by hybridization to the RNA.

The invention is useful in the identification of polypeptides that bind to cellular RNA or viral RNA (see, e.g., proteins identifed in Example 2). The invention is useful for identifying polypeptides that bind to cellular RNA genes, e.g., growth factors, transcription factors, oncogenes, transporters, receptors, translation factors, activators of apoptosis, dendritically localized proteins, etc. (see, e.g., Hellen & Sarnow, *Genes & Dev.* 15:1593–1612 (2001)). The invention is also useful in the identification of polypeptides that bind to viral RNA, e.g., picornaviruses, retroviruses, and flaviviruses (see, e.g., Hellen & Sarnow, *Genes & Dev.* 15:1593–1612 (2001)). Identification of polypeptides that regulate the translation of viral genes is important because translation is typically required for viral replication.

Viral RNAs often form highly structured motifs at their 3' or 5' nontranslated (NTRs) or other regions. These motifs play pivotal roles in viral replication and translation through their interaction with virus encoded proteins as well as essential host factors. Examples of such RNA motifs include the internal ribosome entry sites (IRES), the 3' polypyrimidine tract, and the TAR element of the human immunodeficiency virus (HIV). Identification of host factors that specifically interact with such viral RNA motifs is of great interest in understanding the mechanism of virus replication and in searching for antiviral targets.

The invention specifically demonstrates that polypeptides may be screened from a cellular extract using affinity-labeled RNA sequences derived from the IRES (internal ribosome entry site) Hepatitis C virus (HCV) sequence (see U.S. Pat. No. 5,714,596). IRES sites have been identified in, for example, HCV, HIV, rhinovirus, poliovirus, encephalomyocarditis virus, foot and mouth disease virus, friend murine leukemia virus, Moloney murine leukemia virus, cricket paralysis virus, Kaposi's sarcoma-associated virus and rous sarcoma virus (see, e.g., Hellen et al., *Genes and Dev.* 15:1593–1612 (2001)). IRES sequences can be used from positive stranded ssRNA viruses such as Picornaviridae, e.g., enterovirus (human poliovirus 1, human coxsackie virus B3, bovine enterovirus), rhinovirus (human rhinovirus), hepatovirus (hepatitis A virus), cardiovirus (encephalomyocarditis virus, Theiler's encephalomyelitis virus), aphtovirus (foot-and-mouth disease virus, equine rhinitis A virus, equine rhinitis B virus), and *parechovirus* (human echovirus 22); Cricket paralysis-like virus (i.e., insect picoma like virus) (*plautia stali* intestine virus, *rhopalosiphum padi* virus, cricket paralysis virus); *pestivirus* (bovine viral diarrhea virus, classical swine fever virus, hepatitis C virus), *hepacivirus* (hepatitis C virus, GB virus B); and *Tobamovirus* (crucifer *tobamovirus*); RNA reverse transcribing viruses such as Retroviridae; e.g., *lentivirus* (SIV, HIV), BLV-HTLV retroviruses (human T-lymphotropic virus type 1), and mammalian type C retrovirus (moloney murine leukemia virus, friend murine leukemia virus, Harvey murine sarcoma virus, avian reticuloendotheliosis virus, rous sarcoma virus); and ds DNA viruses such as Herpesviridae, e.g., gammaherpesvirinea (Kaposi's sarcoma-associated *herpesvirus*).

In addition IRES sequences can be used from cellular genes (see, e.g., Hellen et al., *Genes and Dev.* 15:1593–1612 (2001), such as transcription factors, e.g., antennapedia, ultrabithorax, N-myc, c-myc, myt2, AML1/RUNX1, Gtx, c-jun, Mnt, Nkx6.1, NRF, and YAP1; RNA processing factors, e.g., La autoantigen; translation factors; e.g., eIF4GI, TIF4631, and p97/DAP5/NAT1; stress response genes involved in apoptosis, e.g., XIAP, Apaf-1, and BAG-1; stress response chaperone genes, e.g., Bip/GRP78; cellular communication genes, e.g., cyr61, FGF-2, PDGF21c-Sis, and VEGF-A; receptors, e.g., estrogen receptor alpha, IGF-1 receptor, and Notch2; cell junction genes, e.g., connexin 43 and connexin 32; cytoskeleton associated protein genes, e.g., ARC and MAP2; kinases and related genes, e.g., protein kinase p58$^{PITSLRE}$ pim-1, alpha-CaM kinase II, and CDK inhibitor p27; channel and transporter genes, e.g., KV. 14, beta F l-ATPase, Cat-1; and other genes such as ODC, dendrin, neurogranin/RC3, NBS1, FMR1, and RBM3 (see, e.g., Hellen et al., *Genes and Dev.* 15:1593–1612 (2001).

Suitable cellular extracts can be obtained from any primary cell or cell line. For viruses, the cell line is typically one which is competent for viral replication, either naturally or by recombinant means. If the cell is infected with a virus, the virus can be an endogenous virus, an exogenously added virus, or a recombinant construct, e.g., a replicon. In a preferred embodiment, the virus is HCV and the cell extract is from a lymphocyte or a hepatocyte. In one preferred embodiment, the hepatocyte cell line is the Huh7 cell line (see, e.g., Seipp et al., *J. Gen. Virol.* 78:2467–2476 (1997); Rosenberg, *J. Mol. Biol.* 313:451–464 (2001)).

Definitions

An "affinity labeled" molecule, e.g., a nucleic acid, RNA, oligonucleotide, protein, etc., is one that is bound, either covalently, e.g., through a linker or a chemical bond, or noncovalently, through ionic, van der Waals, electrostatic, or hydrogen bonds to a label, e.g., an affinity label. An "affinity label" specifically binds to an "affinity label ligand," allowing isolation and/or purification of the affinity label and/or the molecule(s) to which it is bound. Affinity labels and affinity label ligands typically can be used interchangeably. Preferred affinity labels and their binding partners include biotin/avidin/streptavidin; antibodies/epitopes; protein A or G/antibodies; hexahistidine/nickel; GST/glutathione, etc. The affinity label can be directly bound or indirectly bound (e.g., via a linker) to a probe molecule, e.g., an RNA, for use in identifying RNA binding proteins. The affinity label can be covalently or non-covalently (e.g., hybridized) bound to the probe molecule.

"IRES" or "internal ribosomal entry site" refers to a nucleic acid sequence that directs a ribosome to initiate translation of an RNA molecule. For example, an IRES is found in the 5' untranslated region of an HCV-1 RNA from nucleotide position 20 to 341, and other IRES sequences are known to those of skill in the art, e.g., for HIV, rhinovirus, poliovirus, encephalomyocarditis virus, foot and mouth disease virus, friend murine leukemia virus, Moloney murine leukemia virus, cricket paralysis virus, Kaposi's sarcoma-associated virus and rous sarcoma virus, and in cellular genes such as FGF-2, PDGF, VEGF, c-myc, pim-1, and protein kinase $p_{58}$PITSLRE (see, e.g., Hellen et al., *Genes and Dev.* 15:1593–1612 (2001)). IRES sequences can be identified by examining the deduced or actual secondary structure of an RNA (see, e.g., Kieft et al., *Nat. Struct. Biol.* Apr. 1, 2002 (electronic publication)) and by using functional assays that identify ribosome binding and translation initiation sites.

As used herein, "isolated," or "isolating," when referring to a molecule or composition, such as, for example, an RNA, means that the molecule or composition is separated from at least one other compound, such as other oligonucleotides or other contaminants with which it is associated in vivo, in vitro, or in its naturally occurring state or synthetic state. An isolated composition can also be substantially pure. "Affinity purification" of an RNA or affinity label is a form of "isolating."

A "detectable moiety" is a composition detectable by spectroscopic, photochemical, biochemical, immunochemical, chemical, or other physical means. For example, useful labels include $^{32}p$, fluorescent dyes, electron-dense reagents, enzymes (e.g., as commonly used in an ELISA), digoxigenin, luciferase, CAT, beta galactosidase, GFP, or haptens and proteins which can be made detectable, e.g., by incorporating a radiolabel into the peptide or used to detect antibodies specifically reactive with the peptide.

"Biological sample" includes tissue; cultured cells, e.g., primary cultures, explants, and transformed cells; cellular extracts, e.g., from cultured cells or tissue, whole cell extracts, cytoplasmic extracts, nuclear extracts; blood, etc. Biological samples include sections of tissues such as biopsy and autopsy samples, and frozen sections taken for histologic purposes. A biological sample, including cultured cells, is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

As used herein "oligonucleotides" or "oligomers" refer to a nucleic acid sequence of approximately 5 nucleotides or greater in length, and up to as many as approximately 10, 15, 20, 25, 30, 40, 50, 75, or 100 nucleotides in length. Oligonucleotides are often between about 10 and about 40 nucleotides in length, more often between about 12 and about 35 nucleotides, very often between about 15 and about 30 nucleotides. The terms oligonucleotides or oligomers can also refer to synthetic and/or non-naturally occurring nucleic acids (i.e., comprising nucleic acid analogues or modified backbone residues or linkages).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, y-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

The following eight groups each contain amino acids that are conservative substitutions for one another: 1) Alanine (A), Glycine (G); 2) Aspartic acid (D), Glutamric acid (E); 3) Asparagine (N), Glutamine (Q); 4) Arginine (R), Lysine (K); 5) Isoleucine (1), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. An extensive guide to the hybridization of nucleic acids is found in Tijssen, *Techniques in Biochemistry and Molecular Biology— Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5× SSC, and 1% SDS, incubating at 42° C., or, 5×SSC, 1% SDS, incubating at 65° C., with wash in 0.2×SSC, and 0.1% SDS at 65° C. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

The phrase "modulating," "inhibiting," "treating," "reducing," or "preventing" a disease state (e.g., cancer) or viral (e.g. HCV) infection or disease in the context of assays for compounds affecting disease states, viral replication and/or translation, etc., includes the determination of any parameter that is indirectly or directly under the influence of the disease state or virus. It includes physical, functional and chemical effects, e.g., protein-RNA binding, translation, transcription, genome replication, protein processing, viral particle formation, infectivity, viral transduction, etc. Such functional, chemical or physical effects can be measured by any means known to those skilled in the art.

"Inhibitors," or "modulators" of a disease state or a viral infection or disease (e.g., HCV) refer to inhibitory molecules identified using in vitro and in vivo assays for diseases, viral replication and/or translation inhibition. In particular, inhibitors and modulators refer to compounds that treat, reduce, or prevent disease states and/or viral infection in a subject. Such compounds can be identified using, e.g., using in vitro assays that identify compounds that block binding of proteins to viral or cellular RNA.

To examine the extent of inhibition, samples or assays comprising a viral or cellular RNA are treated with a potential inhibitor compound and are compared to control samples without the test compound. Control samples (untreated with test compounds) are assigned a relative activity value of 100%. Inhibition is achieved when the activity value relative to the control is about 90%, preferably 50%, more preferably 25–0%.

An amount of compound that reduces or inhibits viral replication or translation or RNA-protein binding, as described above, is a "viral modulating amount" of the compound.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

Assays for Cellular Factors that Bind to Viral RNA

The present invention is directed to a method of screening for polypeptides that bind to an RNA molecule. The method comprises incubating an affinity-labeled RNA with a cellular extract, isolating the affinity-labeled RNA and identifying polypeptides bound to the affinity-labeled RNA.

In a preferred embodiment, the affinity-labeled RNA is immobilized on a solid support such as a bead (e.g. agarose or sepharose), a column, a plate, or magnetic bead containing the affinity label ligand. The immobilization is accomplished through the specific binding interaction between the affinity label and the affinity label ligand. The immobilized affinity-labeled RNA is easily and conveniently separated from cellular extract. For example, a filter with pores smaller than the diameter of the bead containing the RNA allows the cellular extract to pass while retaining the beads. Alternatively, the magnetic beads containing the a affinity-labeled RNA may be separated from a solution or mixture by adhering the bead to a magnet such as an electromagnet. Thus, time consuming and complex multi-step purification procedures are reduced to a single step.

After the affinity-labeled RNA is immobilized, washing buffer is passed over the beads or column to wash away the affinity-labeled RNA that has not been immobilized. After washing, the immobilized affinity-labeled RNA is contacted with cellular extract. The cellular extract is incubated with the immobilized affinity-labeled RNA to allow cellular polypeptides to bind to the RNA. After incubation, the cellular extract is washed away leaving the immobilized affinity-labeled RNA that is bound to cellular polypeptides.

Finally, the polypeptides that bound to the immobilized affinity-labeled RNA are analyzed and identified through proteomic techniques known in the art (e.g., mass spectrometry peptide sequencing, two dimensional gel electrophoresis, etc.).

In a preferred embodiment, the cell lysate is derived from a cell that is competent to translate the gene from which the immobilized affinity-labeled RNA is derived.

In one embodiment, the RNA of the present invention is a viral RNA. More preferably, the viral RNA sequence is derived from HC (a flavivirus), HIV (a retrovirus), rhinovirus, poliovirus, encephalomyocarditis virus, foot and mouth disease virus (picornaviruses), friend murine leukemia virus, or rous sarcoma virus or homologous sequences thereof (see, e.g., Hellen & Sarnow, *Genes & Dev.* 15:1593–1612 (2001)). Typically, the viral RNA comprises a 5' untranslated region or a 3' untranslated region. The 5' untranslated region will preferably comprise an IRES sequence. The 3' untranslated region will preferably comprise a polypyrimidine tract.

In a preferred embodiment, the viral RNA comprises an HCV IRES sequence.

In another embodiment, the RNA of the present invention is a cellular RNA. More preferably, the cellular RNA of the present invention encodes a human protein such as, and not limited to, FGF-2, PDGF, VEGF, c-myc, pim-1, and protein kinase p58$^{PITSLRE}$ or homologous sequences thereof (see, e.g., Hellen & Sarnow, *Genes & Dev.* 15:1593–1612 (2001)).

In a preferred embodiment, the RNA is isolated using an affinity label ligand linked to a bead. Preferably, the bead is an agarose bead, a sepharose bead or a bead comprising magnetic materials.

A. Affinity Label Linked to an Amine Moiety of the RNA

In one embodiment, the affinity-labeled RNA comprises an RNA directly or indirectly linked to an affinity label through an amine group of a ribonucleotide base. Typically, the amine group of the ribonucleotide base is covalently linked to the affinity label through an amide bond. Any amine group present on the RNA molecule may be used to from an amide bond. Examples of amine groups on the RNA molecule include, but are not limited to, exocyclic primary amines on guanine and adenine, secondary cyclic amines on adenine, uracil, guanine or cytosine and any primary or secondary amines on RNA base derivatives or backbone derivatives (e.g. primary amines present on phosphoramidite bases). The RNA may be randomly labeled by non-site specific labeling, or specifically labeled by synthesizing the RNA using a base to which the label has already been attached.

In a preferred embodiment, the amide bond between the affinity label and the RNA molecule is formed using an affinity label comprising an amine reactive derivative. Useful amine reactive derivatives include, but are no limited to, succinimidyl or sulfosuccinimidyl esters, cyanogen bromide activated affinity labels and pentafluorophenylesters.

In another preferred embodiment, the amide bond between the affinity label and the RNA molecule is formed using carboxylic acid activating reagents. The affinity label comprising a carboxylic acid is contacted with an activating agent and then coupled to the amine group of the RNA molecule. Useful activating reagents include, but are not limited to carbodiimides (e.g., DCC) and phosphonium and uronium salts (e.g., BOP, PyBOP, HBTU and TPTU).

Affinity labels of the present invention are capable of specifically binding to their ligand molecules such that the affinity labeled RNA may be separated from a mixture or solution. Typically, useful affinity labels are biotin, haptens, peptides, polypeptides and proteins.

In one embodiment, the label can be a biotin molecule. In a preferred embodiment, the label is a biotin-X-succinimidyl ester or -sulfosuccinimidyl ester or a biotin-X-X-succinimidyl ester or -sulfosuccinimidyl ester, wherein X is a seven atom amino hexanoyl linker between the biotin and the reactive carboxylic acid (see, e.g., Molecular Probes Catalogue).

In one embodiment, the affinity label is a peptide epitope. The peptide epitope is capable of specifically binding to its cognate antibody such that the peptide epitope labeled RNA may be separated from a mixture. Examples of peptide epitopes include, but are not limited to, myc, FLAG and influenza hemagglutinin.

In another embodiment, the affinity label is an antibody molecule. The antibody molecule is capable of specifically binding to its cognate epitope such that the antibody labeled RNA may be separated from a mixture. Preferably, the affinity label comprises portions of the Fab region of the antibody without the Fc region.

In another embodiment, the affinity label is a hapten. The hapten is capable of specifically binding to its cognate antibody. Examples of haptens include, for example, digoxigenin, dinitrophenyl-X and fluorophores (e.g., Texas red, fluorescein, rhodamine red, cascade blue and lucifer yellow).

In another embodiment, the affinity label is a polypeptide. Polypeptides useful as affinity labels are capable of specifically binding to their cognate ligand molecule. In a preferred embodiment, the polypeptide affinity label is biotin.

The affinity label may be non-site specifically linked to an amine group of a ribonucleotide base of an RNA molecule. More preferably, the affinity label is site-specifically linked to an amine group of a ribonucleotide base. Site specific affinity labeling is accomplished, for example, by linking the affinity label to a ribonucleotide base before incorporating the base into the RNA chain. One skilled in the art will understand that site-specific linking may serve to avoid or reduce interference with RNA-polypeptide interactions.

In a preferred embodiment, the affinty-labeled RNA label comprises a linker molecule. Linker molecules reduce or avoid interference between the RNA and polypeptide. Linker molecules are well known in the art and include, for example, amino acid linkers, amino hexanoyl linkers, aliphatic carbon chains and oligonucleotide linkers. Typically, the linkers comprise about 5–20 monomeric units. One of skill in the art will understand that the linker may be present in various locations without affecting the utility of the invention. For example, the linker may be between the RNA sequence and the affinity labeled ribonucleotide base or between the affinity labeled ribonucleotide base and the affinity label. In a particularly preferred embodiment, the linker molecule is DNA.

One of skill in the art will recognize that the conditions required to isolate an affinity labeled RNA will depend on the affinity label and affinity label ligand.

B. Affinity Label Linked to a 3' or 5' phosphate group of the RNA

In another embodiment, the affinity-labeled RNA comprises an RNA directly or indirectly linked to an affinity label through a 3' or 5' phosphate group of a ribonucleotide base. The RNA linked to the affinity label is then immobilized and contacted with cell lysate to identify polypeptides that bind to the RNA. The affinity label may be any label described above, e.g., a biotin molecule, a peptide epitope, etc.

In a preferred embodiment, the affinity label is covalently linked to a 3' or 5' phosphate group. Affinity labels containing an amine group are coupled to the 3' or 5' phosphate group using, for example, dithiodipyridine and triphenylphosphine (see, e.g. *Biochemistry* 29:10734 (1990)).

Affinity labels containing a hydroxyl group are linked to the 3' or 5' phosphate group through a phosphodiester bond. Acceptable chemistry methods include, for example, activating agents such as carbodiimides (e.g. DCC) and phosphonium and uronium salts (e.g., BOP, PyBOP, HBTU and TPTU), phosphoramidite chemistry, phosphonate chemistry and triester chemistry.

In a preferred embodiment, the phosphodiester bond is modified to increase the stability of the linkage to cellular phosphatases. Examples of acceptable modifications include, but are not limited to, phosphorothioates, phosphorodithioates, boranophosphates and alkyl phosphonates.

In one embodiment, the affinity label may be linked directly to the 3' or 5' phosphate group of a ribonucleotide base, or via a linker as described above. In one embodiment, the affinity label is a biotin moiety, e.g., biotin-X-cadaverine, wherein X is a $CH_2$ chain or an amino hexanoyl linker (see, e.g., Molecular Probes Catalogue).

In another preferred embodiment, the affinity label comprises an oligonucleotide linker. Typically, the oligonucleotide comprises RNA, DNA, analogs thereof, or a combination of RNA and DNA. One skilled in the art will immediately recognize that various derivatives of RNA and DNA may be used without affecting the utility of the oligonucleotide linker. In a preferred embodiment, the oligonucleotide linker comprises about 1 to about 25 bases.

In another preferred embodiment, the affinity label is linked to a 3' or 5' phosphate group enzymatically. In a preferred embodiment, the enzyme is RNA ligase, which ligates an affinity labeled DNA oligonucleotide or analog thereof to the RNA probe molecule. The DNA oligonucleotide is preferably labeled with a biotin moiety, with or without a linker such as a amino hexanoyl linker or a $CH_2$ linker.

C. Affinity Label Annealed to the RNA

In another embodiment, the affinity-labeled RNA comprises an RNA hybridized to an affinity-labeled oligonucleotide, e.g., a DNA oligonucleotide or analog thereof labeled with a molecule such as a biotin moiety. The RNA annealed to the affinity label is then contacted with cell lysate to identify polypeptides that bind to the RNA.

Annealing the affinity-labeled oligonucleotide to the RNA is facilitated through hybridization (i.e. hydrogen bonding of complementary base strands). One skilled in the art will immediately recognize that annealing conditions will depend upon the degree of complementarity of the RNA and the affinity-labeled oligonucleotide and the length of the complementary region of the affinity-labeled oligonucleotide. Thus, the higher the degree of complementarity and the longer the complementary region of the affinity-labeled oligonucleotide, the greater the potential stringency of the annealing conditions. Preferably, the complementary region is at lease 5 nucleotides, more preferably 10, 15, or 20 nucleotides, up to about 50 nucleotides in length. The affinity labeled oligonucleotide may or may not have a non-hybridized region.

In a preferred embodiment, the length of the affinity-labeled oligonucleotide is at least about 5 nucleotides. In another preferred embodiment, the length of the affinity-labeled oligonucleotide is at least about 2040 nucleotides.

Oligonucleotide Synthesis

Oligonucleotides (DNA, RNA, modified, analogues, and the like) that are used to link the RNA to an affinity label can be made using any suitable method for producing a nucleic acid, such as the chemical synthesis and recombinant methods disclosed herein and known to one of skill in the art.

Chemical synthesis is generally preferred for the production of oligonucleotides or for oligonucleotides and polynucleotides containing nonstandard nucleotides (e.g., probes, primers and antisense oligonucleotides). Direct chemical synthesis of nucleic acids can be accomplished by methods known in the art, such as the phosphotriester method of Narang et al., *Meth. Enzymol.* 68:90 (1979); the phosphodiester method of Brown et al., *Meth. Enzymol.* 68:109 (1979); the diethylphosphoramidite method of Beaucage et al., *Tetra. Lett.*, 22:1859 (1981); and the solid support method of U.S. Pat. No. 4,458,066.

Chemical synthesis typically produces a single stranded oligonucleotide, which may be converted into double stranded DNA by hybridization with a complementary sequence, or by polymerization with a DNA polymerase and an oligonucleotide primer using the single strand as a template. One of skill will recognize that while chemical synthesis of oligonucleotides is often limited to sequences of about 100 or 150 bases, longer sequences may be obtained by the ligation of shorter sequences or by more elaborate synthetic methods.

It will be appreciated that the polynucleotides and oligonucleotides of the invention can be made using nonstandard bases (e.g., other than adenine, cytidine, guanine, thymine, and uridine) or nonstandard backbone structures to provides desirable properties (e.g., increased nuclease-resistance, tighter binding, stability or a desired $T_M$). Techniques for rendering oligonucleotides nuclease-resistant include those described in PCT publication WO 94/12633. A wide variety of useful modified oligonucleotides may be produced, including oligonucleotides having a peptide-nucleic acid (PNA) backbone (Nielsen et at., Science 254:1497 (1991)) or incorporating 2'-O-methyl ribonucleotides, phosphorothioate nucleotides, methyl phosphonate nucleotides, phosphotriester nucleotides, phosphorothioate nucleotides, phosphoramidates. Still other useful oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_n NH_2$ or $O(CH_2)_nCH_3$, where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; etc. Oligonucleotides may also have sugar mirnetics such as cyclobutyls in place of the pentofuranosyl group. Other embodiments may include at least one modified base form or "universal base" such as inosine, or inclusion of other nonstandard bases such as queosine and butosine as well as acetyl-, methyl-, thio- and similarly modified forms of adenine, cytidine, guanine, thymine, and uridine.

The invention further provides oligonucleotides having backbone analogues such as phosphodiester, phosphorothioate, phosphorodithioate, methylphosphonate, phosphoramidite, alkyl phosphotriester, sulfamate, 3'-thioacetal, methylene(methylimino), 3'-N-carbamate, morpholino carbamate, chiral-methyl phosphonates, nucleotides with short chain alkyl or cycloalkyl intersugar linkages, short chain heteroatomic or heterocyclic intersugar ("backbone") linkages, or $CH_2$—NH—O—$CH_2$, $CH_2$—N($CH_3$)—O$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$), or mixtures of the same. Also useful are oligonucleotides having morpholino backbone structures (U.S. Pat. No. 5,034,506).

Useful references include *Oligonucleotides and Analogues, A Practical Approach*, edited by F. Eckstein, IRL Press at Oxford University Press (1991); *Antisense Strategies, Annals of the New York Academy of Sciences*, Volume 600, Eds. Baserga and Denhardt (NYAS 1992); Milligan et al., 9 Jul. 1993, *J. Med. Chem* 36(14): 1923–1937; Antisense Research and Applications (1993, CRC Press), in its entirety and specifically Chapter 15, by Sanghvi, entitled "Heterocyclic base modifications in nucleic acids and their applications in antisense oligonucleotides;" and *Antisense Therapeutics*, ed. Sudhir Agrawal (Humana Press, Totowa, N.J., 1996).

In another example, an oligonucleotide can be made by inserting (ligating) the desired sequence so that it is operably linked to a promoter in a vector (e.g., plasmid). Provided that the promoter and, preferably termination and polyadenylation signals, are properly positioned, the strand of the inserted sequence will be transcribed and act as an oligonucleotide of the invention.

Modulators of RNA-Binding Polypeptides

In a third aspect, the present invention is directed to a method of screening for modulators of RNA-binding polypeptides. The method comprises incubating an affinity-labeled RNA with a cellular extract in the presence of a modulator, isolating the affinity-labeled RNA and identifying polypeptides bound to the affinity-labeled RNA.

By comparing the polypeptides bound o the affinity labeled RNA in the absence and presence of a modulator, the effect of the modulator on the polypeptide RNA-binding activity is determined. For example, if the polypeptide binds to the affinity-labeled RNA in the absence of the modulator but does not bind in the presence of the modulator, then the modulator disrupts the RNA-binding activity of the polypeptide. Likewise, if the polypeptide does not bind to the affinity-labeled RNA in the absence of the modulator but does bind in the presence of the modulator, then the modulator facilitates the RNA-binding activity of the polypeptide.

The chemical compounds of the invention are made according to methodology well known to those of skill in the art. The compounds tested as modulators of viruses or cellular polypeptides for which RNA-binding molecules can be any small organic compound, or a biological entity, such as a protein, peptide, circular peptide, sugar, nucleic acid, or lipid. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art Such combinatorial chemical libraries include, but are not limited to, peptide libraries (see, e.g., U.S. Pat. No. 5,010,175, Furka, Int. J. Pept. Prot. Res. 37:487–493 (1991) and Houghton et al., Nature 354:84–88 (1991)). Other chemistries for generating chemical diversity libraries can also be used. Such chemistries include, but are not limited to: peptoids (e.g., PCT Publication No. WO 91/19735, U.S. Pat. No. 6,153,380), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909–6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217–9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3): 309–314 (1996) and PCT/US96/10287), carbohydrate libraries (see, e.g., Liang et al., Science, 274:1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell is attached a solid phase substrate. In another embodiment, high throughput in vitro assays use, e.g., HCV RNA and protein binding from cellular extracts. Modulators that block binding of the protein to the HCV RNA are thus identified. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; assay screens for up to about 6,000–20,000 different compounds is possible using the integrated systems of the invention.

Administration and Pharmaceutical Compositions

In a fourth aspect, the present invention is directed to a pharmaceutically acceptable composition comprising RNA-binding polypeptides. The compositions are selected by incubating an affinity-labeled RNA with a cellular extract, isolating the affinity-labeled RNA and identifying polypeptides bound to the affinity-labeled RNA in a manner consistent with the first aspect of the invention.

In a fifth aspect, the present invention is directed to a pharmaceutically acceptable composition comprising a modulator of RNA-binding polypeptides. The modulators are selected by incubating an affinity-labeled RNA with a cellular extract in the presence of a modulator, isolating the affinity-labeled RNA and identifying polypeptides bound to the affinity-labeled RNA in a manner consistent with the first aspect of the invention.

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., Remington's Pharmaceutical Sciences, $17^{th}$ ed, 1989).

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials. Injection solutions and suspensions can be prepared from sterile powders, granules, and tablets of the kind previously described.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of viral, e.g., HCV infection, the compounds utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Example 1 describes a method of identifying a polypeptide using an RNA molecule ligated to a biotin labeled DNA oligonucleotide.

HCV IRES RNA (approximately 360 bases) was combined with DNA oligonucleotide (pAACAGCTATGACCAZGAZZGX (SEQ ID NO:1); wherein p is phosphate, Z is biotinylated thymidine and X is 3' terminator), RNA ligase and buffer at 37° C. for 1.5 hours. The RNA ligated to biotin labeled oligonucleotide (heretofore referred to as "ligated RNA") was purified and stored at −80° C. until further use.

Ligated RNA was immobilized on streptavidin agarose beads. The immobilized-ligated RNA was washed with washing buffer (100 mM potassium acetate, 1×PBS, 2.5 mM magnesium acetate). After the wash, the immobilized-tagged RNA was combined with huh7 cell lysate, and reaction buffer (2 mM DTT, 100 mM potassium acetate, 20 mM Tris [pH 7.6]), and 100 U of RNasin at 30° C. for 30 minutes.

Example 2

Example 2 describes a method of identifying a polypeptide using an RNA molecule annealed to a biotin labeled DNA oligonucleotide.

A. Methods

HCV IRES RNA (approximately 360 bases) was combined with DNA oligonucleotide (pCGCTAGCCAGCTTGGGTCTCCCAGX (SEQ ID NO:2); wherein the underlined bases are complementary a portion of the RNA sequence, AG are linker bases, X is biotin with a 15 atom linker, and p is phosphate) in 3 M sodium acetate (pH 5.5) at 94° C. for 30 min. The reaction mix was slowly cooled to room temperature over 3 minutes and incubated at room temperature for 10 minutes. The RNA annealed to biotin labeled oligonucleotide (heretofore referred to as "annealed RNA") was purified and stored on dry ice until further use.

The annealed RNA was immobilized on streptavidin agarose beads. The immobilized-annealed RNA was washed with washing buffer (100 mM potassium acetate, 1×PBS, 2.5 mM magnesium acetate). After the wash, the immobilized-annealed RNA was combined with incubation mix (2 mM DTT, 100 mM potassium acetate, 20 mM Tris, pH 7.6), and 100 U of RNasin at 4° C. for 20 minutes, followed by 3 washes with cold washing buffer and then stored at 94° C.

for 5 minutes in sample buffer. The immobilized-annealed RNA was combined with huh7 cell lysate and incubated at 94° C. for 5 minutes.

B. Results and Discussion

Identified proteins are shown in Table 1. An SDS PAGE was gel used to separate the proteins, identified as difference bands between the hep C IRES lane, and reversed IRES or pcDNA lanes.

DNA fragmentation factor alpha subunit (DFF) is identified in band 5. FF is a natural inhibitor of a pro-apoptotic nuclease, CAD (see Liu et al., *Cell* 9(2): 175–84 (1997). DFF also inhibits other nucleases such as CPAN (Halenbeck et al., *Curr. Biol.* 8(9): 537–40 (1998). The presence of this inhibitor suggests the presence of its cognate nuclease CAD or another DFF-binding protein or nuclease that may be involved in hepatitis C virus IRES function. This nuclease is a potential drug target for inhibition of hepatitis C virus replication or function.

A hypothetical protein (DKFZp434A062.1) is also identified in band 5. This protein has homology to a G-protein coupled receptor.

In bands 1, 2, 3, 4, 5 and 7, a variety of the ribosomal proteins are identified. It is known that the IRES binds 40S ribosomal proteins. However, a number of the ribosomal proteins identified here have not previously been explicitly discovered. These include S19 (band 1), S18 (band 2), S7 (band 3) and an L24 homologue (band 3).

Band 2 contains survival evasion peptide, also known as DSEP, AIDD or preproteolysin. This protein is listed as attenuating retinoic acid responses and promoting the survival of neural cell lines in the Entrez database (gi:15375076). Using EMOTIF, this protein has an alanyl tRNA synthetase signature.

Elongation factor 2 kinase phosphorylates is identified in band 9. EF2 kinase inactivates elongation factor 2 (Pavur et al., *Biochemistry* 39(40): 12216–24 (2000)). This kinase may thus be necessary for inhibition of the translation of RNA into proteins. Although EF2 has been identified as being necessary for IRES translation, EF2 kinase has not been specified as a binding partner of the IRES, or as an important factor in its function. This kinase, which is activated by Ca-calmodulin, has been proposed as one explanation for Ca-dependent inhibition of overall translation, and perhaps regulation of the cell cycle (Ryazanov et al., *New Biol.* 2(10): 843–50 (1990)). The affinity extraction of this kinase with the hep C IRES suggests that it may have some role in translation of this IRES. Its activation (or inhibition of a phosphatase that de-phosphorylates EF2) may be useful for small molecule drugs designed to block IRES translation.

Besides elongation factor 2 kinase and actin, band 9 contains tafazzin. This 292mer contains acyltransferase or glycerol acyltransferase motifs when the sequence is run on the ISREC profile scan server. It is expressed at high levels in muscle and is defective in Barth syndrome, which is characterized by cardiac and skeletal myopathy.

The enzyme inosine monophosphate dehydrogenase (IMPDH) is found in band 10. This enzyme catalyzes the conversion of IMP to XMP, an essential step in the biosynthesis of guanine nucleotides. The antiviral ribavirin blocks IMPDH (Markland et al., *Antimicrob. Agents Chemother.* 44(4): 859–66 (2000)) and thus acts to block hepatitis C infections as well as infections by other viruses. The presence of IMPDH in an affinity extract of the hep C IRES suggests that it may act in an additional mode to facilitate hep C replication.

Band 4 contains the human YVH1 dual specificity phosphatase. Dual specificity phosphatases inactivate target kinases by dephosphorylating S/T and Y residues when phosphorylated, and inactivate MAP kinase family kinases. YVH1 is thought to be localized in the nucleus and is the first tyrosine kinase to contain a zinc finger domain (Muda et al., *J. Biol. Chem.* 274(34): 23991–5 (1999)).

Table 1 Huh7 cell proteins affinity extracted by biotinylated hepatitis C IRES, after separation of the affinity extract on an SDS gel.

TABLE 1

Huh7 cell proteins affinity extracted by biotinylated hepatitis C IRES, after separation of the affinity extract on an SDS gel.

| band | protein | peptides (SEQ ID NO:) | MW app | MW theor |
|---|---|---|---|---|
| 1 | 40S ribosomal protein S19 | 1<br>DVNQQEFVR (3) | 16 kDa | 16.1 kDa |
|   | (dual specificity phosphatase 12 fragment) | 1<br>MTPSSMLTTGR (4) | 16 | 37.7 |
| 2 | 40S ribosomal protein S18 | 2<br>AGELTEDEVER (5), LREDLER (6) | 18 | 17.7 |
|   | survival/evasion peptide | 1<br>ENAGEDPGLAR (7) | 18 | 11.3 |
| 3 | 40S ribosomal protein S7 (S8) | 5<br>HVVFIAQR (8), ILPKPTR (9), VHLDKAQQNNVEHK (10), LLPQLLK (11), ELNITAAK (12) | 22 | 21.9 |
|   | 40S ribosomal protein S5 | 4<br>QAVDVSPLR (13), YLPHSAGR (14), FTPSSFLK (15), ASSPGYIDSPTYSF (16) | 22 | 22.8 |
|   | similar to ribosomal protein L24 | 1<br>AQREQAIR (17) | 22 | 17.7 |

TABLE 1-continued

Huh7 cell proteins affinity extracted by biotinylated hepatitis C IRES, after separation of the affinity extract on an SDS gel.

| band | protein | peptides (SEQ ID NO:) | MW app | MW theor |
|---|---|---|---|---|
| 4 | 40S ribosomal protein S3 | 1 | 32 | 26.7 |
|  |  | GLCAIAQAESLR (18) |  |  |
|  | (dual specificity phosphatase 12) | 1 | 32 | 37.7 |
|  |  | MTPSSMLTTGR (4) |  |  |
|  | (hypothetical protein DKFZp434A062.1) | 1 | 32 | 20.4 |
|  |  | LILLAPGSSTGR (19) |  |  |
| 5 | (DNA fragmentation factor) | 1 | 36 | 45 |
|  |  | SKACDILAIDK (20) |  |  |
|  | (transmembrane protein 7) | 1 | 36 | 25 |
|  |  | PDKGLLPNVLK (21) |  |  |
| 7 | actin | 2 | 45 | 41.7 |
|  |  | RVAPEEHPVLL (22), GYSFTTTAER (23) |  |  |
| 8 | laminin binding protein - similar to | 2 | 47 | 15.5–33.3 |
|  | 40S ribosomal protein SA (P40) | AIVAIENPAD (24), MAANYSSTSTR (25) |  |  |
|  | actin | 4 | 47 | 41.7 |
| 9 | elongation factor 2 kinas, frag.-strong msms | 1 | 49 | 82.2 |
|  |  | RGELDDPEPR (26) |  |  |
|  | actin | 5 | 49 | 41.7 |
|  | (tafazzin) | 1 | 49 | 33.5 |
|  |  | EVLYELIEK (27) |  |  |
| 10 | inosine monophosphate dehydrogenase- msms ok | 1 | ~150 | 55.8 |
|  |  | IKVAQGVSGA (28), VQDKGSIHK (29) |  |  |

We claim:

1. A method of screening for polypeptides that bind to an RNA, the method comprising the steps of:
   (i) incubating an affinity-labeled RNA with a cytoplasmic extract, wherein the RNA is non-covalently linked to an affinity-labeled oligonucleotide;
   (ii) isolating the affinity-labeled RNA; and
   (iii) identifying polypeptides bound to the affinity-labeled RNA.

2. The method of claim 1, wherein the RNA comprises an IRES sequence.

3. The method of claim 1, wherein the RNA is a cellular or a viral RNA.

4. The method of claim 3, wherein the cellular RNA encodes a human protein selected from the group consisting of antennapedia, ultrabithorax, N-myc, c-myc, myt2, AML1/RUNX1, Gtx, c-jun, Mnt, Nkx6.1, NRF, YAP1, La autoantigen, eIF4GI, TIF4631, p97/DAP5/NAT1, XIAP, Apaf-1, BAG-1, Bip/GRP78, FGF-2, PDGF2/c-Sis, VEGF-A, estrogen receptor alpha, IGF-1 receptor, Notch2, connexin 43, connexin 32, Cyr61, ARC, MAP2, protein kinase $p58^{PITSLRE}$, pim-1, alpha-CaM kinase II, CDK inhibitor p27, KV.14, beta F1-ATPase, Cat-1, ODC, dendrin, neurogranin/RC3, NBS1, FMR1, and RBM3.

5. The method of claim 3, wherein the viral RNA is selected from the group consisting of a flavivirus, a retrovirus, a picornavirus, a tombamovirus, and a herpes virus.

6. The method of claim 5, wherein the retrovirus RNA is an HIV RNA.

7. The method of claim 5, wherein the picornavirus RNA is a rhinovirus, a hepatovirus, an enterovirus, a poliovirus, a cardiovirus, an encephalomyocarditis virus, an aphtovirus, a foot and mouth disease virus, or a parechovirus.

8. The method of claim 5, wherein the flavivirus RNA is an HCV RNA.

9. The method of claim 8, wherein the HCV RNA comprises a HCV 5' untranslated region or a HCV 3' untranslated region.

10. The method of claim 9, wherein the 5' untranslated region comprises an HCV IRES.

11. The method of claim 9, wherein the 3' untranslated region comprises a polypyrimidine tract.

12. The method of claim 1, wherein the affinity label is selected from the group consisting of a biotin molecule, a peptide epitope, an antibody molecule, and a hexa-histidine peptide.

13. The method of claim 12, wherein the affinity label is biotin.

14. The method of claim 12, wherein the affinity label is a peptide epitope.

15. The method of claim 14, wherein the peptide epitope is selected from the group consisting of myc, flag, and influenza hemagglutinin.

16. The method of claim 1, wherein the oligonucleotide is a DNA oligonucleotide or a DNA analog oligonucleotide.

17. The method of claim 1, wherein the oligonucleotide is hybridized to the RNA at a complementary region at the 3' end of the RNA.

18. The method of claim 1, wherein the RNA is isolated using an affinity label ligand linked to a bead, a plate or a column.

19. The method of claim 18, wherein the bead is an agarose bead or a magnetic bead.

20. The method of claim 1, wherein the cellular extract is from a cultured human cell.

21. The method of claim 20, wherein the cellular extract is from a hepatocyte cell line.

22. The method of claim 20, wherein the cellular extract is from a lymphocyte cell line.

23. The method of claim 1, wherein the cellular extract is from a human primary cell.

24. The method of claim 23, wherein the cellular extract is from a primary hepatocyte.

25. The method of claim 23, wherein the cellular extract is from a primary lymphocyte.

26. The method of claim 1, wherein the polypeptide is identified by proteolytic digestion and mass spectrometry analysis or in-gel proteolytic digestion and mass spectrometry analysis.

27. The method of claim 1, wherein the oligonucleotide is 5–40 bases in length.

28. A method of screening for polypeptides that bind to an RNA, the method comprising the steps of:
   (i) incubating an affinity-labeled RNA with a cellular extract, wherein an amine group of a ribonucleotide base of the RNA is linked via a linker to a biotin molecule or polypeptide affinity label;
   (ii) isolating the affinity-labeled RNA; and
   (iii) identifying polypeptides bound to the affinity-labeled RNA.

29. The method of claim 28, wherein the affinity label is biotin.

30. The method of claim 28, wherein the polypeptide affinity label is selected from the group consisting of a peptide epitope, an antibody molecule, and a hexa-histidine peptide.

31. The method of claim 30, wherein the polypeptide affinity label is a peptide epitope.

32. The method of claim 31, wherein the peptide epitope is selected from the group consisting of myc, flag, and influenza hemagglutinin.

33. The method of claim 28, wherein the linker molecule is selected from the group consisting of an amino acid linker and an amino hexanoyl linker.

34. The method of claim 28, wherein the RNA comprises an IRES sequence.

35. The method of claim 28, wherein the RNA is a cellular or a viral RNA.

36. The method of claim 35, wherein the cellular RNA encodes a human protein selected from the group consisting of antennapedia, ultrabithorax, N-myc, c-myc, myt2, AML1/RUNX1, Gtx, c-jun, Mnt, Nkx6.1, NRF, YAP1, La autoantigen, eIF4GI, TIF4631, p97/DAP5/NAT1, XIAP, Apaf-1, BAG-1, Bip/GRP78, FGF-2, PDGF2/c-Sis, VEGF-A, estrogen receptor alpha, IGF-1 receptor, Notch2, connexin 43, connexin 32, Cyr61, ARC, MAP2, protein kinase $p_{58}^{PITSLRE}$, pim-1, alpha-CaM kinase II, CDK inhibitor p27, KV.14, beta F1-ATPase, Cat-1, ODC, dendrin, neurogranin/RC3, NBS1, FMR1, and RBM3.

37. The method of claim 35, wherein the viral RNA is selected from the group consisting of a flavivirus, a retrovirus, a picornavirus, a tombamovirus, and a herpes virus.

38. The method of claim 37, wherein the retrovirus RNA is an HIV RNA.

39. The method of claim 37, wherein the picornavirus RNA is a rhinovirus, a hepatovirus, an enterovirus, a poliovirus, a cardiovirus, an encephalomyocarditis virus, an aphtovirus, a foot and mouth disease virus, or a parechovirus.

40. The method of claim 37, wherein the flavivirus RNA is an HCV RNA.

41. The method of claim 40, wherein the HCV RNA comprises a HCV 5' untranslated region or a HCV 3' untranslated region.

42. The method of claim 41, wherein the 5' untranslated region comprises an HCV IRES.

43. The method of claim 41, wherein the 3' untranslated region comprises a polypyrimidine tract.

44. The method of claim 28, wherein the RNA is isolated using an affinity label ligand linked to a bead, a plate or a column.

45. The method of claim 44, wherein the bead is an agarose bead or a magnetic bead.

46. The method of claim 28, wherein the cellular extract is from a cultured human cell.

47. The method of claim 46, wherein the cellular extract is from a hepatocyte cell line.

48. The method of claim 46, wherein the cellular extract is from a lymphocyte cell line.

49. The method of claim 28, wherein the cellular extract is from a human primary cell.

50. The method of claim 49, wherein the cellular extract is from a primary hepatocyte.

51. The method of claim 49, wherein the cellular extract is from a primary lymphocyte.

52. The method of claim 28, wherein the polypeptide is identified by proteolytic digestion and mass spectrometry analysis or in-gel proteolytic digestion and mass spectrometry analysis.

53. A method of screening for polypeptides that bind to an RNA comprising an IRES, the method comprising the steps of:
   (i) incubating an affinity-labeled RNA with a cytoplasmic extract, wherein an amine group of a ribonucleotide base of the RNA is linked to an affinity label, and wherein the RNA comprises an IRES sequence;
   (ii) isolating the affinity-labeled RNA; and
   (iii) identifying polypeptides bound to the affinity-labeled RNA.

54. The method of claim 53, wherein the RNA is an HCV RNA.

55. A method of screening for polypeptides that bind to an RNA comprising an IRES, the method comprising the steps of:
   (i) incubating an affinity-labeled RNA with a cytoplasmic extract, wherein the RNA is non-covalently linked to an affinity-labeled oligonucleotide, and wherein the RNA comprises an IRES sequence;
   (ii) isolating the affinity-labeled RNA; and
   (iii) identifying polypeptides bound to the affinity-labeled RNA.

56. The method of claim 55, wherein the RNA is an HCV RNA.

57. A method of screening for polypeptides that bind to an HCV RNA, the method comprising the steps of:
   (i) incubating an affinity-labeled HCV RNA with a cytoplasmic extract, wherein an amine group of a ribonucleotide base of the RNA is linked to an affinity label;
   (ii) isolating the affinity-labeled RNA; and
   (iii) identifying polypeptides bound to the affinity-labeled RNA.

58. The method of claim 57, wherein the HCV RNA comprises an IRES sequence.

59. A method of screening for polypeptides that bind to an HCV RNA, the method comprising the steps of:
   (i) incubating an affinity-labeled HCV RNA with a cytoplasmic extract, wherein the RNA is non-covalently linked to an affinity-labeled oligonucleotide;
   (ii) isolating the affinity-labeled RNA; and
   (iii) identifying polypeptides bound to the affinity-labeled RNA.

60. The method of claim 59, wherein the HCV RNA comprises an IRES sequence.

61. A method for assaying for compounds that modulate HCV replication and/or translation, the method comprising the steps of:
   (i) incubating an HCV RNA with one or more HCV-RNA binding polypeptides selected from the group consisting of: DNA fragmentation factor (alpha subunit), DFF-binding protein, CAD, and CPAN;
   (ii) contacting the HCV RNA with a test compound; and
   (iii) identifying compounds that bind to the HCV-binding polypeptide or disrupt binding of the HCV-binding polypeptide to the HCV-RNA.

62. The method of claim 61, wherein the test compound is a small organic molecule.

63. The method of claim 61, wherein the test compound is a polypeptide.

* * * * *